Sept. 12, 1961 A. PERRY Plant Pat. 2,089
ROSE PLANT
Filed Aug. 16, 1960
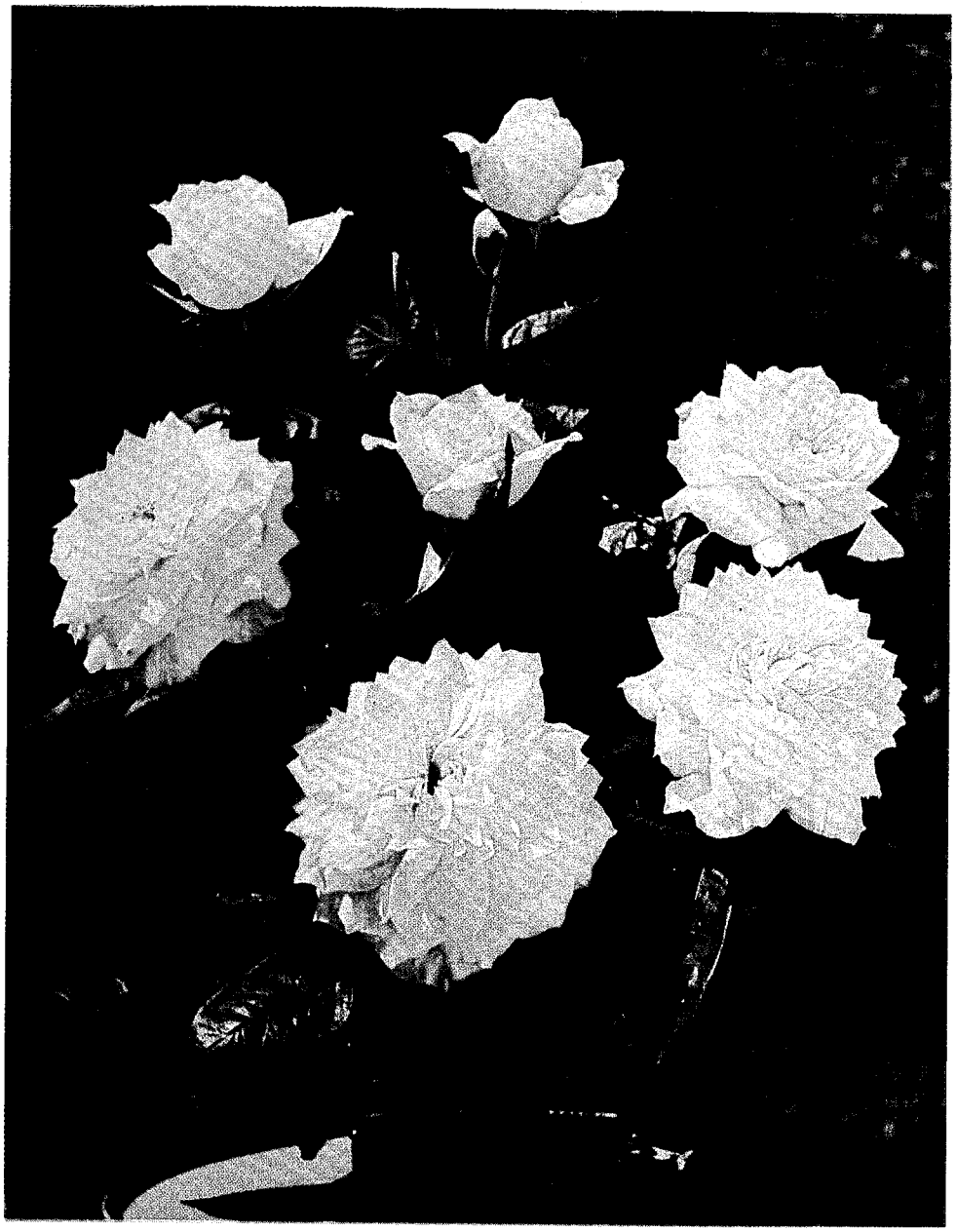
INVENTOR.
ANTHONY PERRY
BY J. F. Cuneo United States Patent Office Plant Pat. 2,089
Patented Sept. 12, 1961

2,089
ROSE PLANT

Anthony Perry, Garden Grove, Calif., assignor to Great Western Rose Company, Inc., Pomona, Calif., a corporation of California Filed Aug. 16, 1960, Ser. No. 50,044
1 Claim. (Cl. 47—61)

This invention relates to a new and distinct variety of rose plant which falls in the hybrid tea class.

The plant resulted by cross-breeding Fred Howard, a patented variety, United States Plant Patent No. 1,006, with Sutter's Gold, a patented variety, United States Plant Patent No. 885, after numerous experiments conducted by me in Garden Grove, California. The original plant was produced by me in 1956, the seed parent was Fred Howard and the pollen parent was Sutter's Gold.

The flowers that are produced by the new variety of rose plant are unique and are distinguished from other varieties in that their color is brighter yellow and the flowers are extremely double. The flowers are produced in abundance during the growing season which normally extends from April to November.

In comparing the blooms of my new variety with those of its seed parent Fred Howard, they are found to be a much brighter yellow color and the plant has a foliage that is much brighter green than the foliage of the seed parent, and the growth habit is much more branched. Compared to its pollen parent Sutter's Gold, it has a flower that is much more double, holds up better when cut, and has a better form of growth with foliage that is closer together and holds to the plant longer.

The new rose belongs to the outdoor bush type and is used principally for cut flowers and for garden ornamentation. The plant has been reproduced asexually by budding performed at Garden Grove, California. The plant and flowers reproduce true with all their distinguishing characteristics, and these distinguishing features are transmitted through succeeding propagations of the variety. The plant will not reproduce true from seed.

The accompanying illustration in color shows a typical specimen of the flowers and foliage. The colors are as correct as it is possible to reproduce them by this type of representation.

A detailed description of the new variety of rose follows, and facilitate identification of the important colors described in this specification, the designation adopted by Maerz and Paul in "A Dictionary of Color" published in 1950, by the McGraw-Hill Book Co. of New York, has been followed.

This new rose belongs to the outdoor bush type and is of the hybrid tea class. Its bright yellow coloration makes it particularly desirable for cut flowers and adds considerable color to any garden.

*The flower*

Locality where grown and observed: Garden Grove, California and at McFarland, California.

Flowers borne: Mainly single with stems approximately sixteen inches long.

Number of blooms: When grown outdoors the plant produces an abundant number of flowers.

Continuity: The plant blooms continuously throughout the blooming season which generally extends from April to November.

Fragrance: The flowers have a slight fragrance in warm weather which becomes much more pronounced in colder weather.

Bud:

*Peduncle.*—Length—average length one half inch, average caliper to heavy. Color—light green inside, darker green outside.

*Before calyx breaks.*—Size—medium, usually one half by five eighths inches. Form—medium length; ovoid; usually with foliacious parts extending beyond the tip of the bud appriximately one quarter of the length of the bud and occasionally more.

*As calyx breaks.*—Color—Plate 9L4. Sepals—pointed; light green inside and dark green outside. The same colors are observed at the base.

*As first petal opens.*—Size—approximately one and three eighths inches by one and three eighths inches. Form—ovate with edges reflexed. Color—outside—Plate 9L4; inside—Plate 9K3. Opening—opens up normally and is not affected abnormally by cold, hot, wet or dry atmospheric conditions.

Bloom:

*Size.*—Average; when fully open, from three and one half to four inches in diameter.

*Petalage.*—Number of petals and petaloids vary from eighty to one hundred twenty, arranged regularly.

*Form.*—High centered and globular at first becoming fully opened. The inner petals vary in size and are slightly curled, being smaller than the outer petals.

Petals:

*Texture.*—Thick and leathery, with the inside of the petals having a somewhat velvety appearance and the outside of the petals having a satiny look.

*Shape.*—Outside—broadly obovate, with average apex being substantially flat with a slight central tip. Intermediate—obovate with apex rounded to flat. Inside—narrowly obovate, somewhat irregular with apex rounded.

(This description of a newly opened flower was taken from a rose grown at McFarland, California, in the month of October.)

*Color.*—Outside petals—Plate 9L5. Intermediate petals—Plate 9L6. Inner petals—Plate 9K9.

A flower that had been open for three days outdoors, in the month of October, at McFarland, California, had substantially the same colors and appearance as a newly opened flower.

The flower has the following general characteristics:

General color effect: Between Forsythia which is Plate 9K6 in the chart, and Golden Glow which is Plate 9L6 in the chart.

Behavior: Petals drop off fairly clean. The flower is not inordinately affected by hot, cold, wet or dry weather. It does, however, fade slightly in extreme heat.

Flower longevity: Cut roses grown outdoors and kept at normal room temperatures last from five to seven days. Flowers on the bush in a garden last from five to seven days.

*Reproductive organs*

Stamens: Average number of stamens varies from 25 to 30. These are arranged regularly about the pistils.

Filaments: These are of medium length, about one quarter of an inch in length. Color—Plate 50L5.

Anthers: Anthers are medium sized and all open approximately at the same time. Color: upper—Lemon Yellow or Plate 10K3; underside—Lemon Yellow or Plate 10K3.

Pollen: Moderate to abundant. Color—Lemon Yellow or Plate 10K3.

Pistils: Pistils average from 40 to 50 in number.

Styles: The styles are moderately even; average length about one quarter inch; average caliper and bunched. Color—Lemon Yellow or Plate 10K3.

Stigma: Color—the color is best described as Salmon Orange.

Ovaries: The ovaries are usually enclosed in the calyx.

Hips:

*Length.*—Average length.

*Form.*—Ovoid generally, about one quarter by one quarter inch; slightly pear shaped.

*Color.*—Dark green outside, somewhat lighter inside.

Seeds: The seeds are of average size but do not set freely.

*The plant*

Foliage:

*Leaves.*—Compound of an average of five leaflets; normal to abundant in quantity. Ovate in shape; approximately one and one half inches wide and two and one half inches in length. Leathery and glossy, margins serrate. Color—dark green, Plate 22F9.

*Leaflets.*—Shape—ovoid with apex acute. Base is round and margins are simply serrate. Color: mature leaves—the upper surface is dark green, Plate 22F9 with the lower side lighter green, Plate 22J4; young leaves—have approximately the same color as mature leaves with a slight red cast.

*Rachis.*—Average size; upper and lower sides are smooth with stipitate glands not prominent.

*Stipules.*—Not prominent.

Disease resistance: This rose plant has exhibited a particularly strong resistance to mildew which is prevalent in California. The resistance to mildew of the novel variety was determined by observation and comparison with varieties of roses that are particularly noted for their resistance to this disease. The varieties used, which are all included in the so-called "All America Winners," were "Chrysler Imperial," United States Plant Patent 1,167; "Charlotte Armstrong," United States Plant Patent 455; "Helen Traubel," United States Plant Patent 1,028; and "Queen Elizabeth," United States Plant Patent 1,259. These were grown by applicant under substantially the same conditions as the new variety.

The test showed the novel variety to have a considerably greater resistance to mildew than "Chrysler Imperial" at the inventor's growing grounds, and showed a better resistance to mildew than either "Charlotte Armstrong" or "Helen Traubel." "Queen Elizabeth" exhibited the best resistance to mildew when tested at the applicant's growing grounds, of all of the listed varieties, and the novel species proved to be at least as resistant to that disease as "Queen Elizabeth."

Growth:

*Habit.*—Upright and well branched. Plant grows from three to four feet tall.

*Growth.*—Hardy and vigorous.

*Canes.*—Medium caliper. Main stems: about eighteen inches long; color—light green, Plate 22J2. Prickles: approximately one quarter of an inch in length; substantially straight; color—vary from reddish to dark brown; hair—none. Small prickles: several; color—vary from reddish to dark brown.

*Branches.*—Color—light green, Plate 22J2. Shape—predominantly vertical. Hair—none. Small prickles—average number about 20 prickles to an eighteen inch stem.

*New shoots.*—Color—light red. Large prickles—about eight prickles to an eight inch stem. Small prickles—none in an eight inch stem.

Having described my invention, I claim:

The new and distinct variety of rose plant of the class designated as hybrid tea roses, substantially as herein shown and described, characterized particularly as to novelty by the distinctive bright yellow color of the flowers, the extremely double petalage of the blooms, the medium size and abundance of the blooms throughout the growing season, the excellent petal substance and the lasting quality of the blooms, the long flower stems, and its vigorous upright growth and the heavy glossy foliage.

No references cited.